United States Patent [19]

Cassinelli et al.

[11] 4,254,110
[45] Mar. 3, 1981

[54] PENTOFURANOSYL ANTHRACYCLINES, INTERMEDIATES IN AND METHOD FOR THEIR PREPARATION AND COMPOSITIONS AND USE THEREOF

[75] Inventors: Giuseppe Cassinelli, Voghera; Federico Arcamone, Nerviano; Aurelio di Marco, Milan, all of Italy

[73] Assignee: Farmitalia Carlo Erba S.p.A., Milan, Italy

[21] Appl. No.: 115,725

[22] Filed: Jan. 28, 1980

[30] Foreign Application Priority Data

Feb. 2, 1979 [GB] United Kingdom ............... 03700/79

[51] Int. Cl.³ ..................... A61K 31/71; C07H 15/24
[52] U.S. Cl. .................................. 424/180; 536/17 A
[58] Field of Search ....................... 536/17 A; 424/180

[56] References Cited

U.S. PATENT DOCUMENTS

| | | | |
|---|---|---|---|
| 4,146,616 | 3/1979 | Penco et al. | 536/17 A |
| 4,181,795 | 1/1980 | Whistler | 536/17 A |
| 4,183,919 | 1/1980 | Cassinelli et al. | 536/17 A |

OTHER PUBLICATIONS

Pigman, "The Carbohydrates", 1957, Academic Press Inc., New York, N.Y., pp. 380-381.
Neller, "Chemistry of Organic Compounds", 3rd Ed., 1965, W. B. Saunders, Co., Philadelphia, Pa., pp. 254-255.
William, "Advances in Carbohydrate Chem. and Biochem.", vol. 31, p. 28, 1975, Academic Press, New York, N.Y.
Gribble et al., J.C.S. Chem. Comm., 1975, p. 535.

*Primary Examiner*—Johnnie R. Brown
*Attorney, Agent, or Firm*—Sheldon Palmer; Peter L. Berger

[57] ABSTRACT

Antitumor anthracycline glycosides of the formula:

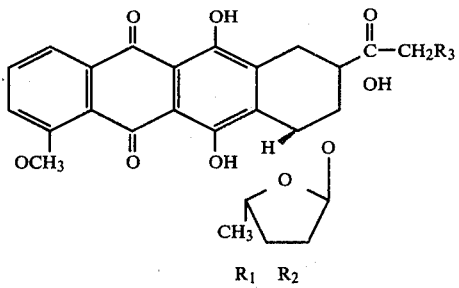

wherein one of $R_1$ and $R_2$ is hydrogen and the other is formyl, hydroxymethyl or aminomethyl, and $R_3$ is hydrogen, hydroxy or an acyloxy group; and pharmaceutically acceptable acid addition salts of said compounds in which one of $R_1$ and $R_2$ is aminomethyl are prepared from daunorubicin, doxorubicin or 14-O-acyl derivatives of doxorubicin by deamination and C-3' epimerization effected with $NaNO_2$ in a cold aqueous acidic medium, such as 1N aqueous acetic acid at 0° C., to give compounds wherein one of $R_1$ and $R_2$ is formyl and the optional further steps of selective reduction, e.g., with $NaCNBH_3$ in 4:1 dioxan:aqueous acetate buffer at pH 4.6 or with $Na(CH_3COO)_3BH$ in benzene under reflux, to form compounds in which one of $R_1$ and $R_2$ hydroxymethyl, or selective reductive amination, e.g., with $NaCNBH_3$ in the presence of methanolic $CH_3COONH_4$ and a dehydrating agent, to form compounds in which one of $R_1$ and $R_2$ is aminomethyl.

9 Claims, No Drawings

PENTOFURANOSYL ANTHRACYCLINES, INTERMEDIATES IN AND METHOD FOR THEIR PREPARATION AND COMPOSITIONS AND USE THEREOF

CROSS-REFERENCE TO RELATED APPLICATIONS

None.

BACKGROUND OF THE INVENTION

1. Field of the Invention

The present invention relates to a new class of anthracyline antitumor antibiotics which are derivatives of daunorubicin (daunomycin), doxorubicin (adriamycin) and 14-O-acyl doxorubicins, methods of making them, certain novel intermediates used in their preparation, the use thereof in treating certain mammalian tumors and compositions containing them.

2. The Prior Art

Daunorubicin and doxorubicin are, of course, both well known antitumor antibiotics which are presently being used in the treatment of various tumors, in some cases with humans.

SUMMARY OF THE INVENTION

The invention provides, in one aspect thereof, a new class of anthracycline antibiotics of the formula:

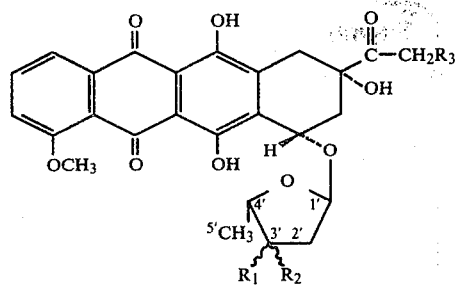

wherein one of $R_1$ and $R_2$ is hydrogen and the other is formyl, hydroxymethyl or aminomethyl, and $R_3$ is hydrogen, hydroxy or an acyloxy group; and pharmaceutically acceptable acid addition salts of said compounds in which one of $R_1$ and $R_2$ is aminomethyl.

In another aspect, the invention provides a method for preparing the compounds of Formula I, the method involving the preparation and use of certain novel intermediates. Generally, according to the method, the anthracycline glycosides of the Formula I, which, depending upon the nature of $R_1$ and $R_2$, contain branched-chain-deoxy- or branched-chain aminodeoxy-sugars, are prepared from known anthracycline glycosides of the Formula II:

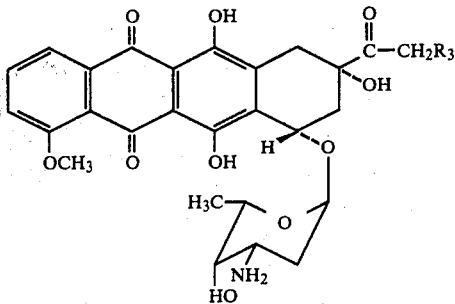

wherein $R_3$ is as defined above, by deamination and C-3' epimerization and, in the case of certain of the compounds, isomerization and/or one of selective reduction and selective reductive amination. The starting anthracycline glycoside compound II in which $R_3$ is hydrogen is daunorubicin. The starting compound in which $R_3$ is hydroxy is doxorubicin and those starting compounds in which $R_3$ is an acyloxy group are 14-O-acyl derivatives of doxorubicin.

In more detail, the invention provides a method for the preparation of compounds of the Formula I in which one of $R_1$ and $R_2$ is hydrogen and the other is formyl. The method comprises reacting a compound of the Formula II with sodium nitrite in a cold (preferably, 0° C.) aqueous acidic medium (preferably, 0.1 N acetic acid). This reaction produces the desired new glycosides which contain a 2,3,5-trideoxy-3'-C-formyl-α-L-pentofuranosyl moiety, as a result of the migration, in a "diazotized intermediate", of the C-5' to the C-3' position and the consequent sugar ring contraction and formation of a 3'-C-formyl branched-chain. The manner of effecting this transformation and its mechanism are described with respect to 3-amino-3-deoxyglycosides by J. M. William, in "Advances in Carbohydrate Chemistry and Biochemistry", Vol. 31, p. 28, 1975, Academic Press, New York, San Francisco and London.

The compounds of the Formula I in which one of $R_1$ and $R_2$ is hydrogen atom and the other is hydroxymethyl are obtained by the further step of selective reduction. The reduction may be effected, for example, with sodium cyanoborohydride in an acidic buffer, preferably, a 4:1 mixture of dioxan:aqueous acetate at pH 4.6, or more preferably with sodium triacetoxyborohydride in benzene according to the method described by G. W. Gribble and D. C. Ferguson in J.C.S. Chem.Comm. 1975, p. 535.

The compounds of the Formula I in which one of $R_1$ and $R_2$ is hydrogen and the other is aminomethyl are obtained by the alternative further step of selective reductive amination with sodium cyanoborohydride in the presence of methanolic ammonium acetate and a dehydrating agent. Preferably, Molecular Sieve (Merck) is used as the dehydrating agent.

In order to facilitate a more complete understanding of the process, the reactions involved therein are set forth in the following reaction scheme:

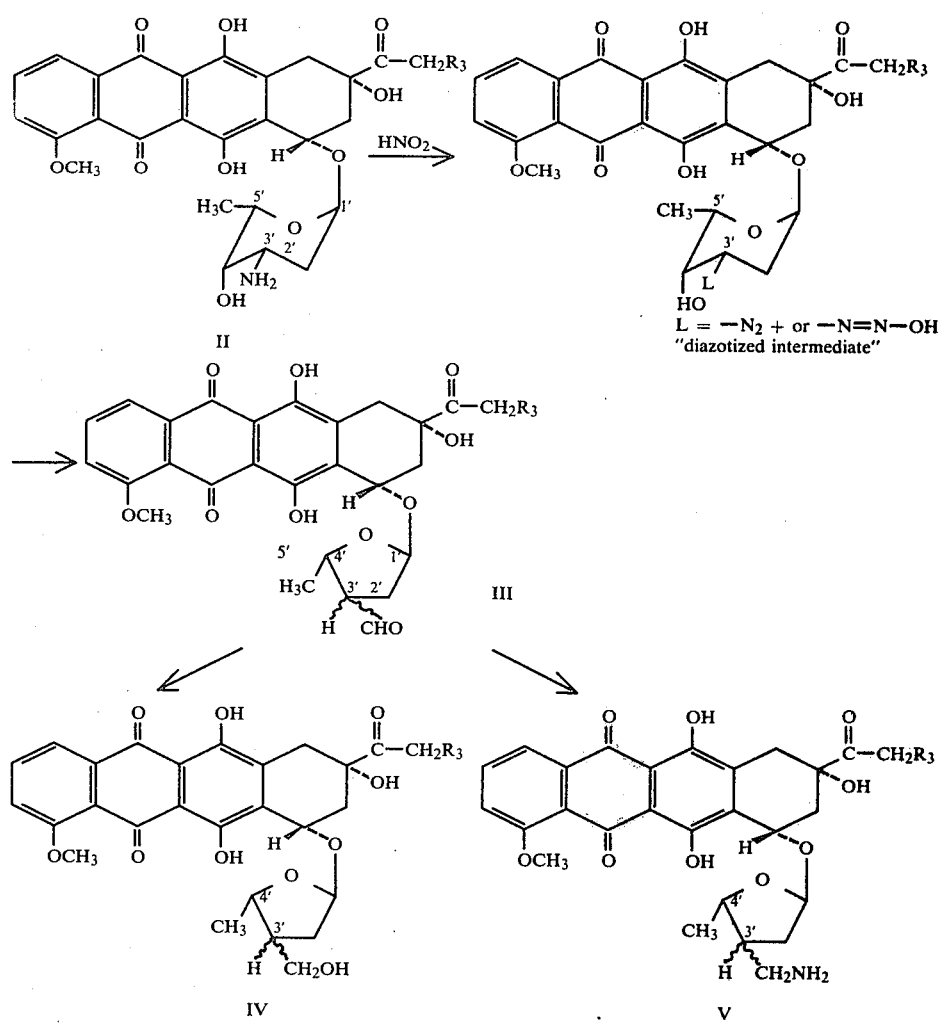

L = —N₂⁺ or —N=N—OH
"diazotized intermediate"

In the case in which the starting compound of the Formula II is daunorubicin, that is, when $R_3$ is hydrogen only one (IIIa) of the two theoretically possible C-3'-epimers is obtained:

This epimer can be readily converted to the other epimer (III-b):

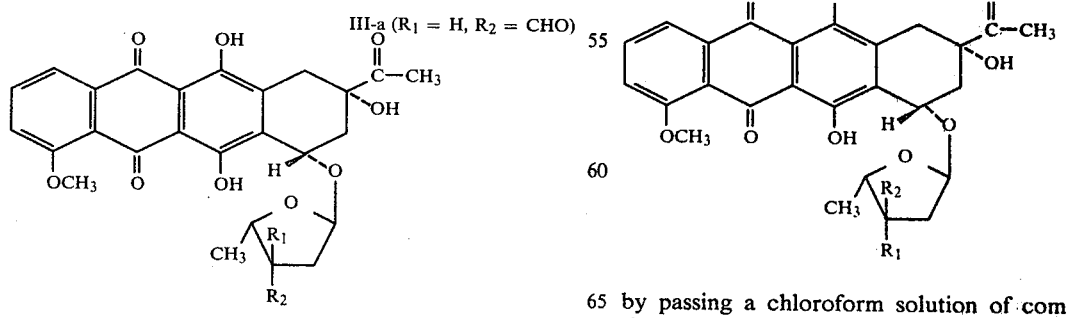

by passing a chloroform solution of compound III-a through a column of silica gel buffered at pH 7.

In yet another aspect thereof, the invention provides the novel diazotized intermediates of the formula:

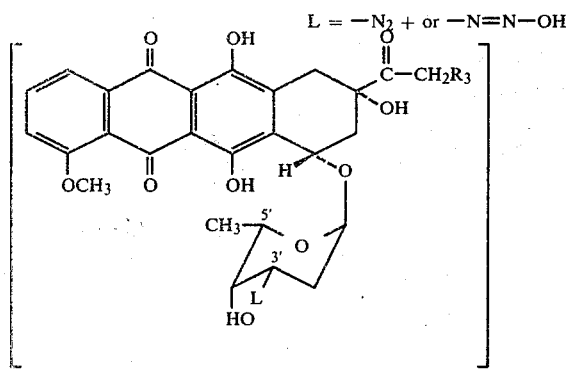

wherein R₃ is as defined above.

In still a further aspect thereof, the invention provides compositions containing and methods for using the compounds of Formula I in treating certain mammalian tumors by administering a therapeutically effective amount of a compound of Formula I, preferably in the form of a composition containing such compound, to a mammal afflicted with a tumor such as P₃₈₈ leukemia.

DESCRIPTION OF THE PREFERRED EMBODIMENTS

The preferred embodiments of the invention are described in the following illustrative examples wherein all parts given are by weight, unless otherwise specified.

EXAMPLE 1

Preparation of
7-O-(2,3,5-trideoxy-3-C-formyl-α-L-threopentofuranosyl)-daunomycinone (III-a)

A solution of 4.5 g (8 mmol) of daunorubicin hydrochloride (II: R₃=H) in 200 ml of water was cooled to 0° C. and then treated with 2.76 g (80 mmol) of sodium nitrite and 80 ml of 1 N aqueous acetic acid in several portions over a period of 20 minutes with stirring at a rate such the temperature did not exceed 0° C. After 3 hours at 0° C., the reaction mixture, which contained a red precipitate, was brought to room temperature and, after bubbling nitrogen therethrough to remove the excess nitrous acid, was filtered. The red precipitate was washed with water and then dissolved in chloroform. The chloroform solution, after being dried over magnesium sulphate and evaporated to a small volume, yielded, upon the addition of petroleum ether, 4 g of compound (IIIa) as a red powder. m.p. 179°–180° C. (dec.) $[\alpha]_D^{23°} = +178°$ (c=0.04 in CHCl₃). U.V. and VIS spectra: $\lambda_{max}^{CH3OH}$ 233, 252, 290, 480, 496 and 530 nm (E₁ $_{cm}^{1\%}$ 643, 463, 156, 227, 232 and 134). Field desoprtion mass spectrum: m/e 510 (M⁺) and 398. P.M.R. spectrum (CDCl₃): 1.38 (d, CH₃—C-4'), 2.43 (s, CH₃CO), 4.11 (s, CH₃O), 5.32 (broad s, C—7—H), 5.87 (broad s, C—1'—H). 7.2-8.1 (m, three aromatic protons), 9.78 (d, CHO), 13.16 and 13.89 δ (two s, two phenolic protons).

13C-NMR (acetone-d₆): 16.6 (CH₃—C-4'); 24.1 (C-14); 33.1 (C-10); 33.3 (C-2'); 35.5 (C-8); 52.7 (C-3'); 56.4 (O—CH₃); 68.9 (C-7); 75.4 (C-4'); 76.7 (C-9); 106.2 (C-1'); 111.4 (C-5a, C-11a); 119.5 (C-4a, C-1, C-3); 134.7 (C-10a, C-12a); 135.3 (C-6a); 136.0 (C-2); 155.6 (C-11); 156.4 (C-6); 161.5 (C-4); 186.9 (C-5, C-12); 191.7 (CHO); 211.5 (C-13).

EXAMPLE 2

Conversion of Compound (III-a) into the corresponding 3'-epimer (III-b)

A solution of 2 g of compound (III-a) in 20 ml of chloroform was chromatographed on a column of silica gel buffered at pH 7 (M/15 phosphate buffer) and eluted with a 98:2 chloroform-acetone mixture to give 1.5 g of pure compound (III-b). Compound (III-b) can be readily distinguished from the starting compound (III-a) by thin layer chromatography. Compound (III-a) has an Rf of 0.25 and compound (III-b) has an Rf of 0.20 with a 95:5 chloroform:acetone mixture. They can also be distinguished by their chemical and physical properties. m.p. (III-b) 120° C. (dec.) $[\alpha]_D^{23°} = +246°$ (c=0.05 in CH₃OH). U.V. and VIS spectra: $\lambda_{max}^{CH3OH}$ 233, 252, 290, 480 496 and 530 nm. Field desorption mass spectrum: m/e 510 (M⁺) and 398. P.M.R. spectrum (CDCl₃): 1.40 (d, CH₃—C-4'), 2.46 (s, CH₃CO), 4.11 (s, CH₃O), 5.19 (broad s, C-7—H), 5.84 (broad s, C-1'—H), 7.2-8.1 (m, three aromatic protons), 9.71 δ (d, CHO), 13.14 and 13.94 δ (two s, two phenolic protons), 13C-NMR (acetone-d₆): 20.4 (CH₃—C-4'); 24.1 (C-14); 32.8 (C-10); 34.3 (C-2'); 35.8 (C-8); 56.4 (O—CH₃); 57.2 (C-3'); 68.5 (C-7); 74.3 (C-4'); 76.6 (C-9); 106.5 (C-1'); 111.2 (C-11a, C-5a); 119.4 (C-4a, C-1, C-3); 134.9 (C-10a, C-12a); 135.2 (C-6a); 136.0 (C-2); 155.6 (C-11); 156.6 (C-6); 161.5 (C-4); 186.4 (C-5); 186.8 (C-12); 201.8 (CHO); 211.8 (C-13).

EXAMPLE 3

Preparation of
7-O-(2,3,5-trideoxy-3-C-formyl-α-pentofuranosyl)-adriamycinone (III: R₃=OH)

The preparation of the title compound was performed according to the procedure described in Example 1, starting from doxorubicin hydrochloride (II: R₃=OH). The compound was obtained as a red powder having a m.p. of 150° C. (dec.) $[\alpha]_D^{23°} = +269°$ (c, 0.05, in CHCl₃). U.V. and VIS spectra: $\lambda_{max}^{CH3OH}$ 233, 253, 480, 496 and 530 nm (E₁ $_{cm}^{1\%}$ 620, 460, 222, 225 and 140). Field desorption mass spectrum m/e 526 (M⁺) and 414. P.M.R. spectrum (CDCl₃): 1.41 (d, CH₃—C-4'), 4.13 (s, CH₃O), 4.85 (broad s, COCH₂—O—), 5.38 (broad s, C-7—H), 5.87 (broad s, C-1—H), 7.2-8.1 (m, three aromatic protons), 9.80 (d, CHO), 13.01 and 13.96 δ (two s, two phenolic protons).

EXAMPLE 4

Preparation of
7-O-(2,3,5-trideoxy-3-C-hydroxymethyl-α-L-threopentofuranosyl)-daunomycinone To a solution of 510 mg, 1 mmol of compound (III-a) in 80 ml of dioxan and 20 ml of an 0.2 N aqueous acetate buffer at pH 4.6 there was added portion-wise with stirring, 500 mg; 8 mmol of sodium cyanoborohydride at room temperature. After 3 hours the reaction mixture was diluted with water and extracted with chloroform. The chloroform extract was washed with water, dried over sodium sulphate, concentrated to a small volume under reduced pressure and chromatographed on a column of silica gel buffered at pH 7 (M/15 phosphate buffer). Elution was performed with a 99:1 chloroform-:methanol mixture to give the title compound in pure form. m.p. 157°–161° C. (dec.) $[\alpha]_D^{23°} = +286°$ (c=0.05, in CH₃OH). U.V. and VIS spectra: λ$_{max}$-

$^{CH3OH}$ 234, 253, 290 480, 496 and 530 nm (E$_1$ $_{cm}$$^{1\%}$ 600, 494, 118, 208, 212, 120). Field desorption mass spectrum: m/e 512 (M+) and 398.

13C-NMR (CDCl$_3$): 122.13 (C-1); 139.26 (C-2); 123.38 (C-3); 164.65 (C-4); 100.03 (C-5); 160.12 (C-6); 72.09 (C-7); 40.13 (C-8); 80.70 (C-9); 36.90 (C-10); 159.51 (C-11); 190.27 (C-12); 216.37 (C-13), 28.59 (C-14); 60.34 (OCH$_3$-4); 124.45 (C-4a); 138.08, 138.46 (C-6a, C-10a, C-12a); 114.86, 114.77 (C-5a, C-11a); 109.50 (C-1'); 38.64 (C-2'); 40.11 (C-3'); 79.50 (C-4'); 19.65 (C-5'); 65.94 (C-6').

The title compound can be distinguished from the starting compound (III-a) by thin layer chromatography using a 4:1 chloroform:acetone mixture as the eluent (III-a) has an Rf=0.55 while the title compound has an Rf=0.25.

EXAMPLE 5

Preparation of 7-O-(2,3,5-trideoxy-3-C-hydroxymethyl-α-L-threopentofuranosyl)-daunomycinone A benzene suspension of 8 equivalents of sodium borohydride was refluxed with 6.5 equiv. of glacial acetic acid for 15 minutes under a nitrogen atmosphere to give a clear solution of sodium triacetoxyborohydride. To this solution was added a benzene solution of 510 mg; 1 mmol of compound (III-a) and the mixture was refluxed for 1 hour. The reaction mixture was then diluted with water and extracted with chloroform. The further work-up and column chromatographic purification described in Example 4 were carried out, to give the title compound as characterized in Example 4. The yield according to this procedure was higher than in Example 4.

EXAMPLE 6

Preparation of 7-O-(2,3,5-trideoxy-3-C-aminomethyl-α-L-pentofuranosyl-daunomycinone (V: R$_3$=H)

To a solution of 1.02 g, 2 mmol of compound (III-a) in 16 ml of dry dioxan was added a solution of 1.32 g of ammonium acetate in 72 ml of anhydrous methanol and 4 g of Molecular Sieve. The mixture was then treated with 0.1 g of sodium cyanoborohydride. After three hours under stirring at room temperature the reaction mixture was diluted with water and the slightly acidic solution (pH 5.2) was extracted with chloroform in order to remove the starting material and some lipophilic impurities. The aqueous phase was brought to pH 7.2 with sodium hydrogen carbonate and then extracted with chloroform. The chloroform extract, after being concentrated was chromatographed on a column of silica gel buffered at pH 7 (M/15 phosphate buffer). Elution was effected with a 89.5:10:0.5 chloroform:methanol:water mixture to give some fractions containing the title compound in pure form. The fractions were pooled and diluted with water. The organic phase was washed with water, dried over anhydrous sodium sulphate and concentrated to a small volume under vacuum. Treatment with an equivalent of hydrochloric acid in methanol followed by precipitation with diethyl ether gave the title compound in pure form as the hydrochloride. m.p. 160°–165° C.(dec.) $[\alpha]_D^{23°}=+211°$ (c=0.02 in CHCl$_3$) $\lambda_{max}^{CH3OH}$ 235, 254, 290, 480, 495 and 530 nm. Field desorption mass spectrum: m/e 511 (M+), 398 and 362.

BIOLOGICAL ACTIVITY

The cytotoxic activity of several of the new compounds according to the invention were tested against HeLa cells in vitro (time of exposure to the compounds=24 hours) in comparison with daunorubicin and doxorubicin. The obtained results are shown in Table 1.

TABLE 2

| Effect on HeLa cells viability in vitro | |
|---|---|
| Compound | ID$_{50}$ (ng/ml) |
| Daunorubicin . HCl | 7.4 |
| Compound III-a | 320 |
| Compound III-b | 1.750 |
| Compound IV (R$_3$ = H) | 1.600 |
| Doxorubicin . HCl | 10 |
| Compound III (R$_3$ = OH) | 140 |

The antitumor activity of the same compounds was tested against P-388 leukemia in mice. The test results are given in Table 2. As can be seen from the data in Table 2, Compounds III (R$_3$=OH), III-a and IV (R$_3$=H) at the tolerated doses (100~200 mg/Kg) have an antitumor activity which is higher than or comparable to those of both daunorubicin and doxorubicin.

TABLE 2

| Effect against P-388 leukemia in mice | | | |
|---|---|---|---|
| Compound | Dose$^{(a)}$ mg/Kg | T/C % | Toxic Deaths$^{(b)}$ |
| Daunorubicin . HCl$^{(c)}$ | 2.9 | 169 | 0/37 |
| | 4.4 | 167 | 0/38 |
| | 6.6 | 157 | 19/38 |
| III-a$^{(d)}$ | 50 | 168 | 0/8 |
| | 100 | 163 | 0/5 |
| | 200 | 190 | 2/5 |
| III-b$^{(e)}$ | 50 | 110 | 0/10 |
| | 100 | 110 | 0/10 |
| | 200 | 125 | 0/9 |
| IV (R$_3$ = H)$^{(e)}$ | 50 | 130 | 0/7 |
| | 100 | 160 | 0/6 |
| | 200 | 220 | 0/5 |
| Doxorubicin . HCl$^{(c)}$ | 4.4 | 195 | 0/17 |
| | 6.6 | 206 | 0/17 |
| | 10.0 | 244 | 4/18 |
| III-(R$_3$ = OH)$^{(e)}$ | 50 | 163 | 0/9 |
| | 100 | 190 | 0/9 |
| | 200 | 231 | 1/7 |

$^{(a)}$Mice were treated i.p. on day 1 after tumor cell inoculation.
$^{(b)}$Evaluated on the basis of macroscopic autoptic findings.
$^{(c)}$Injected as a water solution.
$^{(d)}$Injection as a 5% aqueous ethanol suspension.
$^{(e)}$Injected as a 1:9 Tween 80 : water suspension.

Variations and modifications can, of course, be made without departing from the spirit and scope of the invention.

Having thus described our invention what we desire to secure by Letters Patent and hereby claim is:

1. An anthracycline glycoside of the formula:

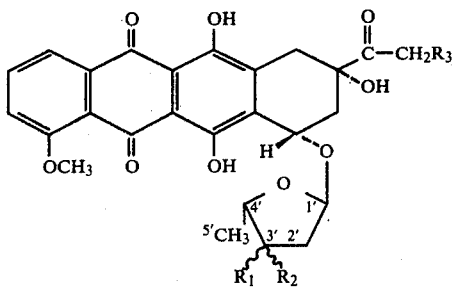

wherein one of $R_1$ and $R_2$ is hydrogen and the other is formyl, hydroxymethyl or aminomethyl, and $R_3$ is hydrogen or hydroxy; and the hydrochlorides of said compounds in which one of $R_1$ and $R_2$ is aminomethyl.

2. An anthracycline glycoside as claimed in claim 1, wherein $R_1$ is hydrogen, $R_2$ is formyl and $R_3$ is hydrogen; the sugar moiety having the configuration:

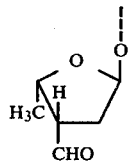

3. An anthracycline glycoside as claimed in claim 1, wherein $R_1$ is hydrogen, $R_2$ is formyl and $R_3$ is hydrogen; the sugar moiety having the configuration:

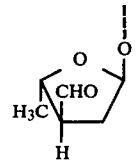

4. An anthracycline glycoside as claimed in claim 1, wherein one of $R_1$ and $R_2$ is hydrogen and the other is formyl and $R_3$ is hydroxy.

5. An anthracycline glycoside as claimed in claim 1, wherein one of $R_1$ and $R_2$ is hydrogen and the other is hydroxymethyl and $R_3$ is hydrogen.

6. An anthracycline glycoside as claimed in claim 1, wherein one of $R_1$ and $R_2$ is hydrogen and the other is aminomethyl and $R_3$ is hydrogen.

7. A diazo compound of the formula:

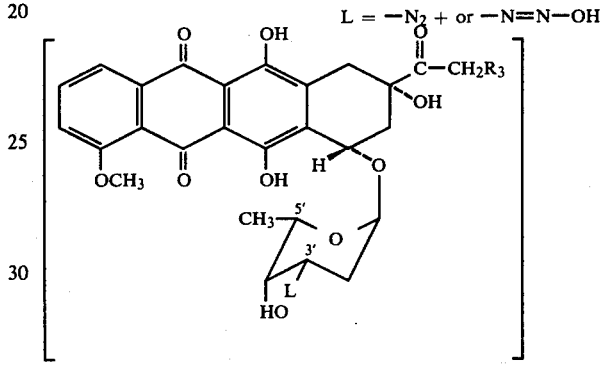

wherein $R_3$ is hydrogen or hydroxy and L is a diazo group.

8. A pharmaceutical composition for inhibiting the growth of P388 leukemia comprising a therapeutically effective amount of an anthracycline glycoside as claimed in claim 1 in combination with an inert carrier therefor.

9. A method of inhibiting the growth of $P_{388}$ leukemia comprising intraperitoneally administering to a mammal afflicted therewith, a therapeutically effective amount of an anthracycline glycoside as claimed in claim 1.

* * * * *